US009250253B2

(12) United States Patent
Markin

(10) Patent No.: US 9,250,253 B2
(45) Date of Patent: Feb. 2, 2016

(54) SYSTEM AND METHOD FOR ANATOMICAL PATHOLOGY SAMPLE HANDLING, STORAGE, AND ANALYSIS

(75) Inventor: Rodney S. Markin, Omaha, NE (US)

(73) Assignee: Prairie Ventures, L.L.C., Omaha, NE (US)

( * ) Notice: Subject to any disclaimer, the term of this patent is extended or adjusted under 35 U.S.C. 154(b) by 1047 days.

(21) Appl. No.: 13/034,958

(22) Filed: Feb. 25, 2011

(65) Prior Publication Data

US 2011/0207169 A1    Aug. 25, 2011

Related U.S. Application Data

(60) Provisional application No. 61/307,876, filed on Feb. 25, 2010.

(51) Int. Cl.

| G01N 1/30 | (2006.01) |
|---|---|
| B01L 99/00 | (2010.01) |
| B01L 3/00 | (2006.01) |
| C12M 1/00 | (2006.01) |
| G01N 21/00 | (2006.01) |
| A61B 5/00 | (2006.01) |
| G01N 35/00 | (2006.01) |
| B01L 3/02 | (2006.01) |
| G01N 1/31 | (2006.01) |
| G01N 35/10 | (2006.01) |

(52) U.S. Cl.
CPC ........ *G01N 35/00009* (2013.01); *B01L 3/0227* (2013.01); *B01L 3/505* (2013.01); *G01N 1/31* (2013.01); *G01N 1/312* (2013.01); *B01L 2200/141* (2013.01); *B01L 2300/021* (2013.01); *B01L 2300/0812* (2013.01); *B01L 2300/123* (2013.01); *G01N 35/00029* (2013.01); *G01N 2001/317* (2013.01); *G01N 2035/1086* (2013.01); *Y10T 436/25* (2015.01)

(58) Field of Classification Search
CPC ............. G06N 1/28; G06N 1/30; G06N 1/31; G06N 1/36; G06N 2001/31; G06N 2001/362; G06N 1/312; G06N 35/00009; G06N 2035/1086; B01L 3/505; B01L 3/0227; B01L 2200/141; B01L 2300/021; B01L 2300/123; B01L 2300/0812; Y10T 436/25; G91N 35/00029
See application file for complete search history.

(56) References Cited

U.S. PATENT DOCUMENTS

| 3,939,019 A * | 2/1976 | Pickett ........................... 156/57 |
|---|---|---|
| 5,135,313 A | 8/1992 | Bowman |
| 5,351,801 A | 10/1994 | Markin et al. ............. 198/346.1 |
| 5,366,062 A | 11/1994 | Markin et al. ............. 198/345.3 |
| 5,370,215 A | 12/1994 | Markin et al. ............. 198/346.1 |
| 5,377,813 A | 1/1995 | Markin et al. ............. 198/465.1 |
| 5,402,875 A | 4/1995 | Markin et al. ............. 198/346.1 |
| 5,417,922 A | 5/1995 | Markin et al. .................. 422/65 |
| 5,427,743 A | 6/1995 | Markin ......................... 422/104 |
| 5,510,984 A | 4/1996 | Markin et al. ........... 346/424.02 |
| 5,529,166 A | 6/1996 | Markin et al. ................ 198/349 |
| 5,567,386 A | 10/1996 | Markin ........................... 422/65 |
| 5,589,137 A | 12/1996 | Markin et al. ................ 422/104 |
| 5,614,415 A | 3/1997 | Markin ........................... 436/48 |
| 5,800,780 A | 9/1998 | Markin ........................... 422/65 |
| 5,985,670 A | 11/1999 | Markin ........................... 436/47 |
| 6,068,437 A | 5/2000 | Boje et al. ................ 414/331.02 |
| 2007/0026530 A1 | 2/2007 | Wu et al. |
| 2009/0181449 A1 | 7/2009 | Markin ...................... 435/286.1 |

FOREIGN PATENT DOCUMENTS

| EP | 1186543 | 3/2002 |
|---|---|---|
| KR | 10-2007-0022975 | 2/2007 |
| KR | 10-2010-0001730 | 6/2010 |

OTHER PUBLICATIONS

Cross, S. S. et al. "Offline telepathology diagnosis of colorectal polyps: a study of interobserver agreement and comparison with glass slide diagnoses." Journal of Clinical Pathology (2002) 55 305-8.*

Lowe, Henry J. et al. "Building a medical multimedia database system to integrate clinical information: an application of high-performance computing and communications technology." Bull. Med. Libr. Assoc. (1995) 83 57-64.*

* cited by examiner

*Primary Examiner* — Christopher A Hixson
(74) *Attorney, Agent, or Firm* — Tyson B. Benson; Advent, LLP

(57) ABSTRACT

A carrier strip having a plurality of areas for retaining anatomical pathology specimens may have a backing, a cover coupled to the backing along side regions located along opposite longitudinal edges of the carrier strip and along lateral intermediate regions positioned between each of the plurality of areas for retaining anatomical pathology specimens. The carrier strip may be configured to individually retain each of the anatomical pathology specimens in one of the plurality of areas for retaining anatomical pathology specimens between the backing and the cover. Diagnostic studies of anatomical pathology specimens may be facilitated by distributing a digital copy of an image of the specimen may be to a pathologist. A diagnosis may be received from the pathologist based on the digital image of the specimen.

10 Claims, 4 Drawing Sheets

SYSTEM AND METHOD FOR ANATOMICAL PATHOLOGY SAMPLE HANDLING, STORAGE, AND ANALYSIS

CROSS REFERENCE TO RELATED APPLICATION

This application is a continuation of and claims the benefit of and priority to U.S. Provisional Patent Application No. 61/307,876 filed Feb. 25, 2010, entitled SYSTEM AND METHOD FOR ANATOMICAL PATHOLOGY SAMPLE HANDLING, STORAGE, AND ANALYTICAL, which document is hereby incorporated by reference to the extent permitted by law.

BACKGROUND

The present invention relates to methods of preparing anatomical pathology specimens for study. In particular, the invention relates to methods of preparing histopathology specimens that are conducive to automated processes and more efficient storage.

The preparation of histological specimens from surgically obtained tissue generally includes fixation, dehydration, clearing, and infiltration of the specimen. Chemical fixation is often applied to prevent degradation of the specimen and allow for later long term storage. An alternative to chemical fixation is frozen section fixation in which a specimen is quickly frozen, sectioned and prepared so that evaluation of the specimen can be done in quickly, at times while the patient is still in surgery. The invention disclosed in the present application is envisioned as being most compatible with chemically fixated specimens, but may be used with frozen section samples as well.

After fixation of the specimen has been done to preserve the specimen, it may be dehydrated, cleared, and infiltrated. Because specimens will often be prepared in blocks of material and then sliced or sectioned for study, the specimens must be made sufficiently rigid to allow for sectioning. In this process, the specimen is dehydrated with application of a water miscible stripping agent such as ethanol. The ethanol is then cleared from the specimen by application of a hydrophobic clearing agent such as xylene. The specimen may then be infiltrated with a matrix material, such as paraffin wax or epoxy resin, to provide a block in which the specimen is suspended. The block may then be sectioned by a technician and the sections mounted for analysis by a pathologist.

Traditionally, prepared specimens are mounted to glass or quartz microscope slides for analysis. The slides are fragile and must be transported and stored accordingly. This requires slides to be packaged in cassettes that results in a large amount of wasted space. Accordingly, it is an object of the present invention to provide a system for high density storage of prepared histology specimens. It is a further object of the present invention to provide for an automated system for cataloging stored samples and digital images thereof to facilitate analysis of the specimens by a remotely located pathologist. It is yet another object of the present invention to provide a system of peer review of histological diagnoses provided by one or more pathologists.

SUMMARY

Some aspects of the invention relate to a carrier strip having a plurality of areas for retaining anatomical pathology specimens the carrier strip having a backing, a cover coupled to the backing along side regions located along opposite longitudinal edges of the carrier strip and along lateral intermediate regions positioned between each of the plurality of areas for retaining anatomical pathology specimens. The carrier strip may be configured to individually retain each of the anatomical pathology specimens in one of the plurality of areas for retaining anatomical pathology specimens between the backing and the cover.

Other aspects of the present invention relate to method of handling anatomical pathology specimens including placing a specimen on a specimen carrier strip backing. The specimen may then be stained and covered with a cover material. The cover material may then be coupled to the carrier strip backing to form a carrier strip having a plurality of anatomical pathology specimens disposed.

Yet other aspects of the invention relate to methods of facilitating diagnostic studies of anatomical pathology specimens. Such methods include imaging an anatomical pathology specimen and storing a digital image of the specimen in a memory. A digital copy of the digital image of the specimen may be distributed to a pathologist. A diagnosis may be received from the pathologist based on the digital image of the specimen.

DETAILED DESCRIPTION

The following detailed description of the invention references the accompanying drawing figures that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

Figure 1:
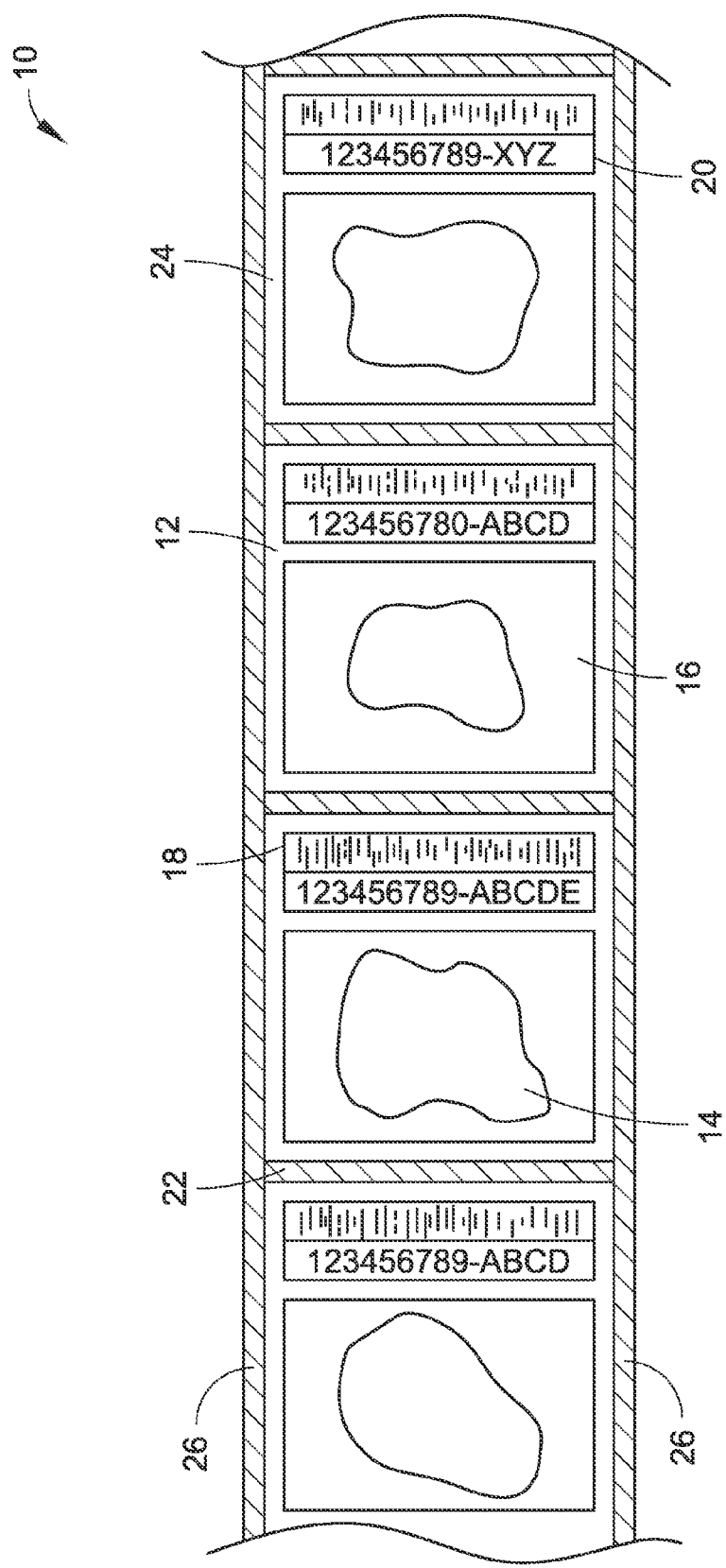
FIG. 1 is an elevation view of a specimen carrier strip.

Turning now to the drawing figures, and particularly to FIG. 1, a specimen carrier strip 10 includes a backing 12 for supporting a biological specimen 14 shown as an infiltrated histology section. In some embodiments, biological specimen 14 may be a surgical pathology specimen disposed within a specimen block portion 16 that may be made of paraffin or other suitable material. A unique machine readable identifier 18 may be provided for each biological specimen 14. The machine readable identifier may be a one or two dimensional barcode, or any other machine readable identifier. In addition to the machine readable identifier 18, an alphanumeric identifier 20 may also be provided so a human technician can manually verify the identity of a biological specimen. While shown as a strip running laterally across strip 10, the identifiers may be placed longitudinally along a side. When more than one identifier is used, they may be positioned next to one another, as shown, or placed in different areas.

Figure 2:
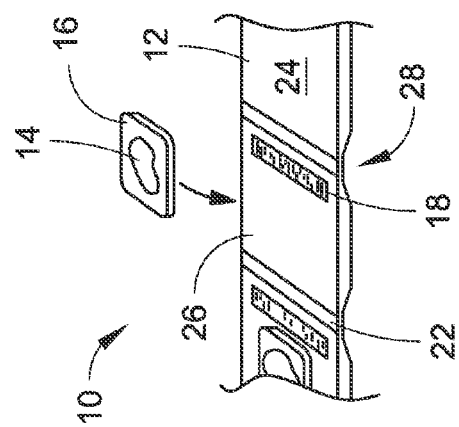
FIG. 2 is a partial perspective view of a sample carrier strip.

Strip 10 is segregated into multiple specimen regions 24 by intermediate regions 22. Intermediate regions 22 may comprise a seam or region of thinned carrier material (as shown in FIG. 2) to allow for bending of strip 10 at intermediate regions 22. Each specimen region 24 provides space for both biological specimen 14 and a specimen identifier (i.e. machine readable identifier 18 or alphanumeric identifier 20). Side regions 26 are along either longitudinal edge of strip 10. One or both of side regions 26 may be provided with apertures, slots, notches, dimples, or other features to facilitate proper indexing of strip 10 in relation to a piece of machinery. In other embodiments, an indexing feature may be positioned in intermediate regions 22. A cover material may be attached to backing 12. The cover may be adhered, fused, or otherwise coupled to backing 12 at regions 22 and 26 to enclose and cover biological specimen 14.

Referring to FIG. 2, a specimen carrier strip 10 includes a backing 12 for supporting biological specimen 14 that is contained in a specimen block portion 16. Intermediate region 22 is shown as being a thinned region 28 of backing 12. Backing 12 may have an adhesive or other means for coupling block portion 16 to region 24. In general, an anatomical pathology technician would prepare the specimen block 16 and place it in region 24 of strip 10. A machine could then scan the machine readable identifier 18, or the technician could manually enter an identifier into a computer database. This identifier could be used to identify the specimen and tie it to a specific patient through an electronic health record or laboratory information system.

Figure 3:
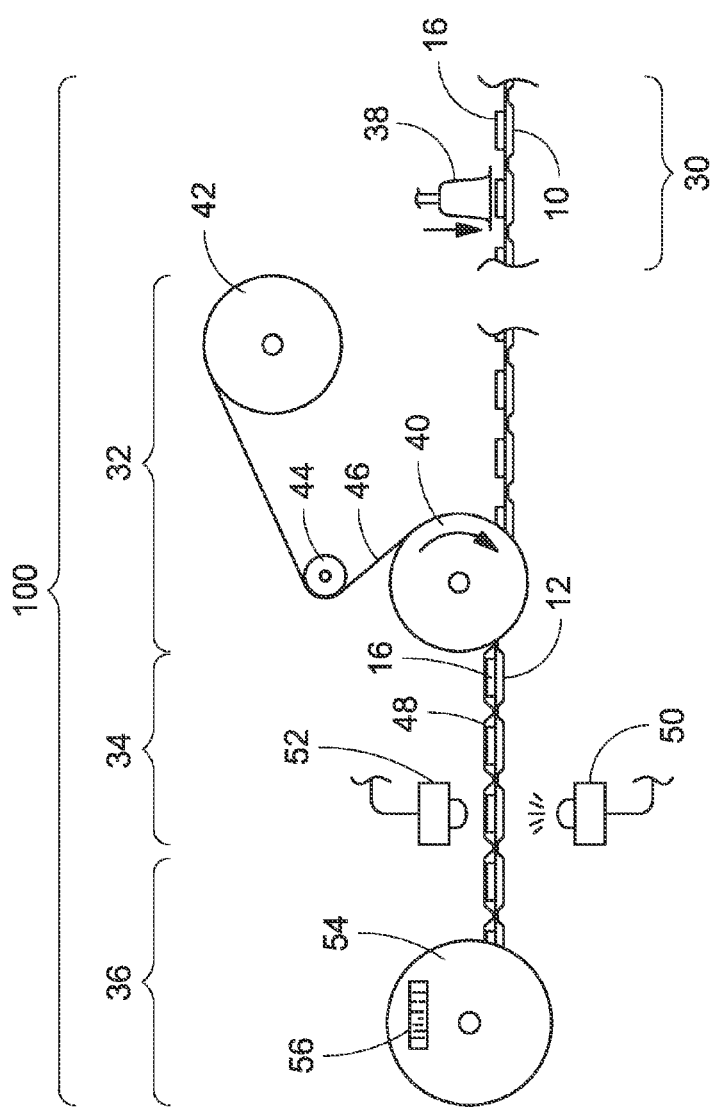
FIG. 3 is a schematic view of a sample evaluation system.

Referring to FIG. 3, a specimen evaluation system 100 may include a specimen staining subsystem 30, a covering subsystem 32, an imaging subsystem 34 and a storage subsystem 36. Strip 10 is fed to staining subsystem 30 where a staining device 38 is used to apply a stain to individual biological specimens 14. The system may be configured to allow for different stains to be applied to adjacent biological specimens 14 on strip 10. Strip 10 may be fed to specimen evaluation system 100 by any of a variety of passive or driven conveyors or combinations of such conveyors. When a biological specimen 14 is positioned under staining device 38, staining device 38 may be lowered to prevent the migration of stain to other specimens. When staining device is in place, one or more of a variety of staining compounds may be applied, including biological stains such as antibodies or chemical stains including dyes and pigments. After the stain has been applied, staining device 38 may be raised to allow strip 10 to be indexed forward and position a new biological specimen 14 under staining device 38. In alternative embodiments, a variety of emersion baths containing solvated stains may be provided. The position of the baths relative to strip 10 may be changed such that one area 24 is positioned above a bath and may then be submerged to apply stain to biological specimen 14. Strip 10 may be passed through a mild heating zone or maintained at room temperature to facilitate drying of any stain solvent that may be present.

After stain has been applied to the biological specimens, strip 10 may be advanced to a covering subsystem 32. Cover subsystem 32 may include a roller 40, cover material spool 42, and a guide roller 44. Cover material 46 may be wound on spool 42 and fed over guide roller 44. Roller 40 may draw cover material 46 and laminate or otherwise couple cover material 46 to base 12 along continuous strip 10. As strip 10 is drawn past roller 40, each region 24 includes a biological specimen disposed within a specimen block portion 16 and positioned between backing 12 and cover 48.

After covering, strip 10 is advanced to imaging subsystem 34. In a basic form, imaging subsystem 34 includes a light source 50 and a high resolution imaging device 52. Light source 50 is shown below backing 12 with imaging device 52 positioned above cover 48. Alternatively, these positions could be reversed. To allow light transmission through strip 10 and to imaging device 52, backing material 12 and cover 48 are sufficiently transparent to allow for high resolution imaging of biological specimen 14. Many conventional materials may be used including polyesters (such as polyethylene terephthalate, i.e. MYLAR), polyacrylates, epoxys, polyolefins, and other polymer materials that are sufficiently transparent while allowing for a construction of backing 12 that can support specimen block portion 16 and flex in region 22. In other embodiments, backing 12 may comprise more than one material. In such embodiments a transparent, rigid material may be used in region 23, while a more flexible material may be used in region 22. Such embodiments may lack thinned region 28.

A variety of lighting sources may be used depending on the diagnostic testing being done. For example, if a fluorescent stain is used, the light source may be selected to have a higher emission at or near the excitation frequency for the stain. When an image is captured, it will generally include substantially all of region 24 such that the biological specimen and the identifier (i.e. machine readable identifier 18 and/or alphanumeric identifier 20) are captured together. The captured image may be a digital image which may be stored in an image database or other memory. In some embodiments, it may be advantageous to have multiple images taken of the same biological specimen with the same or multiple imaging devices.

After imaging, strip 20 may be fed to a storage subsystem 36. Storage system 56 comprises a storage spool 54. As strip 10 is fed to storage spool 54, strip 10 flexes in regions 22 to wrap around spool 54. When spool 54 has reached its capacity it may be placed in a specimen library that would provide for high density storage of the specimens. Each spool may be identified with an identifier 56 which could, in turn, be associated with all the specimens on storage spool 54. Alternatively, segments of strip 10 may be cut and the strips stacked and boxed for storage. This would provide another option for high density storage of specimens.

Conventional glass microscope slides are typically used for specimen examination and storage. Such slides are typically three inches long and one inch wide. With the use of strip 10, each biological specimen would only require an area one inch long by one inch wide because additional area on ether side of biological specimen 14 would not be necessary for handling. Also, conventional slides are made of glass or quartz which can be very brittle and easily broken. With the use of strip 10, other more resilient materials may be utilized.

Figure 4:
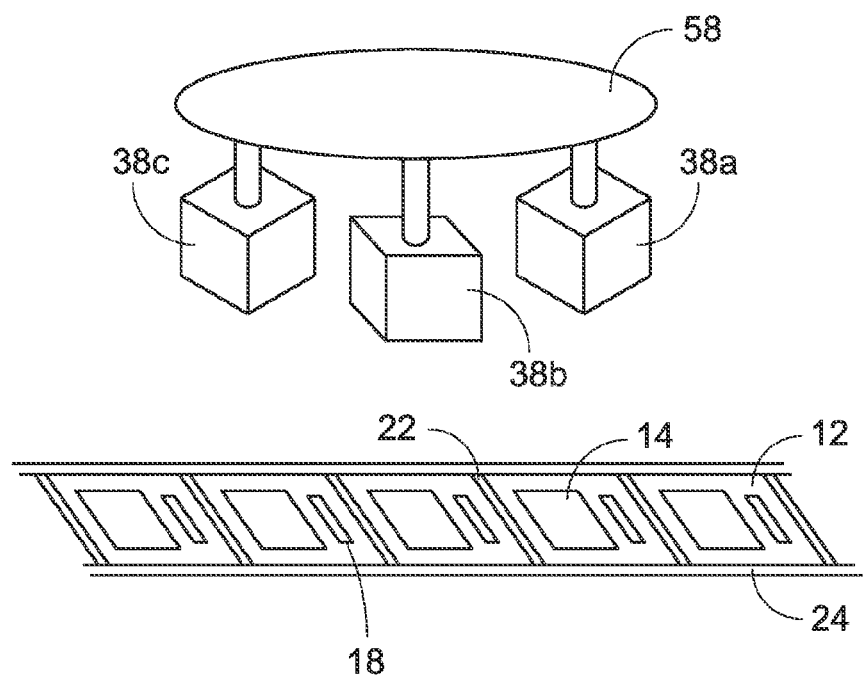
FIG. 4 is a perspective view of a multi head staining subsystem.

Referring to FIG. 4, a multi head staining subsystem is provided. In the embodiment shown, the staining device may include three heads 38a, 38b, and 38c extending from a base 58. Base 58 may be rotated to align one of the three heads 38 over a biological specimen 14 on strip 10. When the appropriate head 38 is aligned over a biological specimen 14, base 58 and heads 38 may be lowered so that biological specimen 14 is substantially covered by one of heads 38. A stain may then be applied to the individual biological specimen. After application of the stain, base 58 and heads 38 may be raised away from strip 10. In some embodiments, base 58 and heads 38 may be moved laterally away from strip 10 such that rotation of base 58 is done away from strip 10. In this way, no biological specimen would ever pass under more than one of heads 38 thereby preventing unwanted stain migration.

Figure 5:
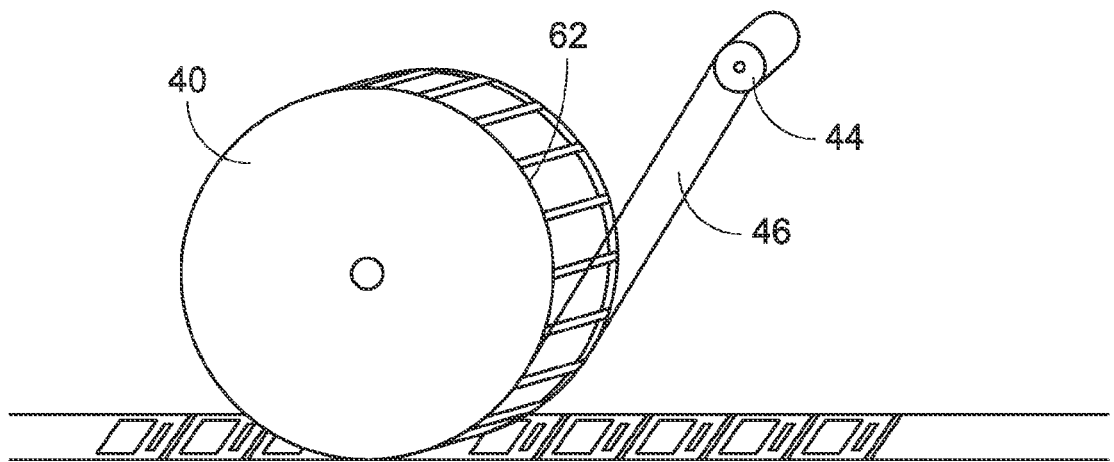
FIG. 5 is a perspective view of a covering subsystem.

Referring to FIG. 5, a covering subsystem may include a roller 40 and a guide roller 44. Guide roller 44 maintains the angel at which cover material 46 is supplied to roller 40 while the diameter of spool 42 (shown in FIG. 3) reduces. Roller 40 is driven at the same rate at which strip 10 is advanced. Roller 40 includes edges 60 and 62 that contact regions 24 of strip 10 and cross portions 64 that contact each region 22 as strip 10 advances. Edges 60 and 62, and cross portions 64 may be provided to couple cover material 45 to strip 10 in one or more of a variety of ways including pressure fusing, partial melting, ultrasonic welding, adhesive lamination, or any other suitable method.

Figure 6:
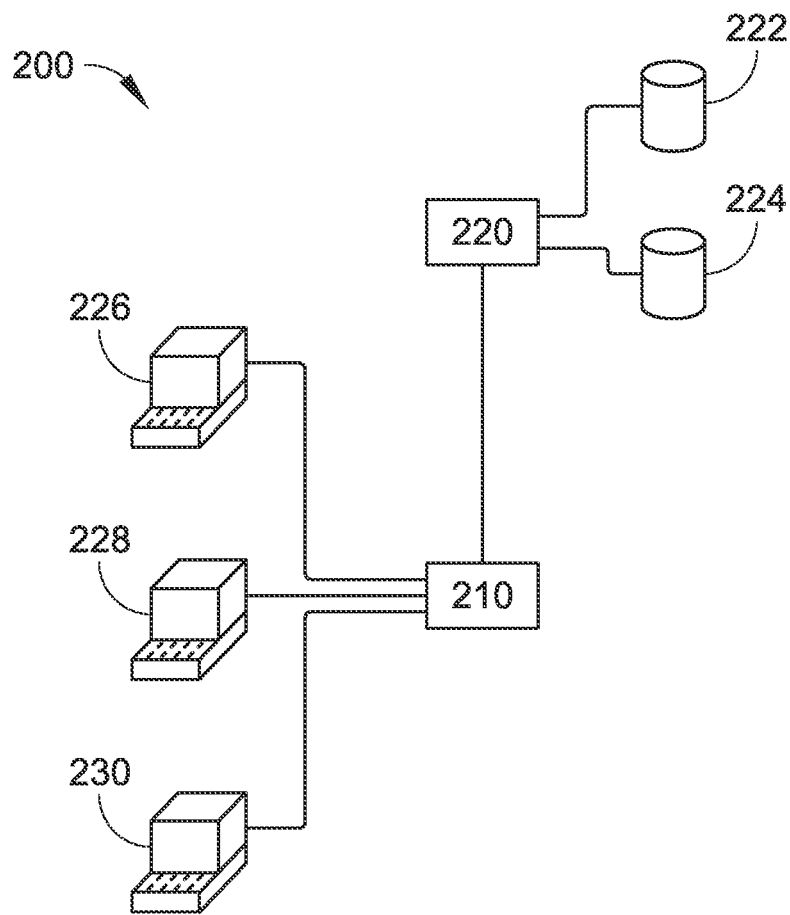
FIG. 6 is a schematic view of a computerized system for storing, distributing, and analyzing images of anatomical pathology specimens.

Referring to FIG. 6, a computerized system for storing, distributing, and analyzing images of anatomical pathology specimens 200 is provided. The system includes a subsystem 210 which is utilized to route images and electronic health record information through system 200. Subsystem 210 could be a subsystem operated by a healthcare provider with an anatomical pathology lab, or it could be operated by a third party. Subsystem 220 is utilized to link image data from image database 222 to an electronic health record database 224. Subsystem 220 may be a laboratory information system, and electronic health record system or a combination of both. Subsystem 210 may be used to route images to remote locations 226, 228, and 230 where the images may be examined by a pathologist without the need to evaluate the actual anatomical specimens. A report form may be provided with the images to the pathologist. Alternatively, the pathologist may be able to view images and fill in reports using a web based application. When the pathologist has completed a pathology report, subsystem 210 can provide that information to an electronic health record system for inclusion in the patient's electronic health record.

In some embodiments, subsystem 210 may include additional functionality to permit the evaluation of the various pathologists who may perform diagnostic studies based on images provided through a credibility test. In such embodiments, a credibility score may be assigned to one or more of the various pathologists according to one of a variety of known credibility testing techniques. One such embodiment includes the distribution of the same images to several pathologists and determining a consensus diagnosis. Variations from the consensus would be tracked and pathologists who most frequently vary from consensus diagnoses could be deselected for referral of future pathology studies. Additionally, subsystem 210 could be used to determine if a pathological diagnosis provided varies from a subsequent diagnosis provided in the patient's electronic health record. In some embodiments the credibility score could be calculated as the percentage of diagnostic studies performed by a particular pathologist in which that pathologist's diagnosis agreed with the consensus diagnosis.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that relative terms are intended to encompass different orientations of the device in addition to the orientation depicted in the Figures.

Moreover, it will be understood that although the terms first and second are used herein to describe various features, elements, regions, layers and/or sections, these features, elements, regions, layers and/or sections should not be limited by these terms. These terms are only used to distinguish one feature, element, region, layer or section from another feature, element, region, layer or section. Thus, a first feature, element, region, layer or section discussed below could be termed a second feature, element, region, layer or section, and similarly, a second without departing from the teachings of the present invention.

It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Further, as used herein the term "plurality" refers to at least two elements. Additionally, like numbers refer to like elements throughout.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow. The scope of the disclosure is not intended to be limited to the embodiments shown herein, but is to be accorded the full scope consistent with the claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims.

What is claimed is:

1. A method of handling anatomical pathology specimens comprising:
  positioning a specimen carrier strip to receive a specimen block portion including a specimen, the specimen comprising an infiltrated histology specimen, the specimen carrier strip comprising multiple specimen regions segregated by intermediate regions, respective specimen regions comprising a specimen carrier strip backing for receiving the specimen, respective intermediate regions comprising a region of thinned carrier material configured to allow for bending of the specimen carrier strip at the respective intermediate regions;

placing the specimen block portion on the specimen carrier strip backing, the specimen block portion comprising a paraffin material, the carrier strip backing comprising a transparent material to allow for high resolution imaging of the specimen;

positioning a first specimen carrier strip backing of the specimen carrier strip under a staining device, the first specimen carrier strip having a first specimen block portion disposed thereon, the first specimen carrier strip including a first specimen, positioning the staining device such that the staining device is proximate to the first specimen, the staining device comprising a plurality of heads extending from a base, the plurality of heads configured to rotate about the base, each head of the plurality of heads configured to dispense a stain;

applying a first stain to the first specimen disposed within the first specimen block portion;

raising the staining device such that the staining device is distal to the first stained specimen disposed within the first specimen block portion;

transitioning the staining device laterally with respect to the first stained specimen;

rotating the base of the staining device while the staining device is laterally transitioned with respect to the first stained specimen;

positioning a second specimen carrier strip backing of the specimen carrier strip under a staining device, the second specimen carrier strip having a second specimen block portion disposed thereon, the second specimen carrier strip including a second specimen, positioning the staining device such that the staining device is proximate to the second specimen disposed;

applying a second stain to the second specimen disposed within the first specimen block portion, the second stain different from the first stain;

raising the staining device such that the staining device is distal to the second stained specimen disposed within the second specimen block portion;

covering the second stained specimen, via a cover subsystem, with a cover material;

coupling the cover material with the carrier strip backing to form a carrier strip having a plurality of stained specimens disposed therein;

obtaining a digital image of the first stained specimen and the second stained specimen via an imaging subsystem, the imaging subsystem comprising an imaging device for capturing an image of the first stained specimen and the second stained specimen and a light source configured to emit light having an emission characteristic at or near an excitation frequency of at least one of the first stain or the second stain;

storing the digital image of the first stained specimen as a data structure in an electronic health record database;

electronically distributing, via a computerized subsystem, the digital image of the first stained specimen to a plurality of pathologists to perform a diagnostic study of the first stained specimen;

receiving a plurality of electronic reports from respective pathologists of the plurality of pathologists, the electronic report comprising an evaluation of the respective pathologist corresponding to the first stained specimen;

storing the plurality of electronic reports as a data structure in the electronic health record database;

calculating, via the computerized subsystem, a consensus diagnosis corresponding to the first stained specimen based upon the plurality of electronic reports;

deselecting, via the computerized subsystem, a pathologist of the plurality of pathologists based upon a diagnostic study variance of the pathologist with respect to a consensus diagnosis of the plurality of pathologists, wherein deselecting of the first pathologists comprises causing the first pathologist to be deselected for referral of future pathology studies.

2. The method of claim 1, wherein the specimen is an infiltrated histology section.

3. The method of claim 1, further comprising performing a credibility test whereby pathologists may be rated relative to one another on the of the accuracy of their respective diagnostic studies.

4. A method of facilitating diagnostic studies of anatomical pathology specimens comprising:

placing an anatomical pathology specimen on a specimen carrier strip backing;

positioning a first specimen carrier strip backing under a staining device, positioning the staining device such that the staining device is proximate to the specimen disposed within the first specimen carrier strip backing, the staining device comprising a plurality of heads extending from a base, the plurality of heads configured to rotate about the base to align with a respective specimen, each head of the plurality of heads configured to dispense a stain;

applying a stain to the anatomical pathology specimen disposed within the first specimen carrier strip backing;

raising the staining device such that the staining device is distal to the specimen disposed within the first specimen carrier strip backing;

transitioning the first specimen carrier strip backing such that a second specimen carrier strip is positioned under the staining device;

imaging, via an imaging subsystem, the stained anatomical pathology specimen, the stained anatomical pathology specimen disposed on a carrier strip;

storing a digital image of the stained anatomical pathology specimen in at least one of a database or a memory;

distributing, via a computerized subsystem, a digital copy of the digital image of the stained anatomical pathology specimen to a plurality of pathologists;

receiving, via the computerized subsystem, a pathological diagnosis from at least one of the plurality of pathologists based on the digital image of the stained anatomical pathology specimen;

determining, via the computerized subsystem, a consensus diagnosis based upon the pathological diagnosis; and deselecting, via the computerized subsystem, a first pathologist from the plurality of pathologists based upon a diagnostic study variance of the first pathologist with respect to the consensus diagnosis, wherein deselecting of the first pathologists comprises causing the first pathologist to be deselected for referral of future pathology studies.

5. The method of claim 4, further comprising:

determining a credibility of at least one of the pathologists relative to at least one other of the plurality of pathologists through determination of credibility scores.

6. The method of claim 5, further comprising distributing copies of the digital image, via a computerized subsystem, to at least one pathologist of the plurality of pathologists based upon a credibility score of the at least one pathologist, wherein the digital image is distributed after determination of the credibility score.

7. The method of claim 6, wherein the credibility score of the at least one pathologist is calculated based on a percentage of diagnostic studies in which the diagnosis of the at least one pathologist agreed with a consensus diagnosis reached by those of the plurality of pathologists.

8. The method as recited in claim 1, further comprising transitioning the first specimen carrier strip backing such that a second specimen carrier strip is positioned under the staining device.

9. The method of claim 1, further comprising determining a consensus diagnosis based upon the diagnostic study of the specimen.

10. The method of claim 1, wherein at least one electronic report of the plurality of reports is generated through a web-based user-interface application.

\* \* \* \* \*